US005882942A

United States Patent [19]
Kagaya

[11] Patent Number: 5,882,942
[45] Date of Patent: *Mar. 16, 1999

[54] METHOD FOR SAMPLING FECES

[75] Inventor: Etsuro Kagaya, Tokyo, Japan

[73] Assignee: Wako Pure Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 593,374

[22] Filed: Jan. 29, 1996

[30] Foreign Application Priority Data

Feb. 15, 1995 [JP] Japan ................................. 7-049266

[51] Int. Cl.$^6$ ............................................ G01N 1/00
[52] U.S. Cl. .................... 436/174; 436/66; 422/58; 422/61; 422/99; 422/102; 422/104
[58] Field of Search ............................ 422/99, 100, 101, 422/102, 103, 104, 58, 61; 436/66, 174; 73/864.41

[56] References Cited

U.S. PATENT DOCUMENTS

| | | | |
|---|---|---|---|
| 4,108,162 | 8/1978 | Chikashige et al. | 128/2 B |
| 4,978,504 | 12/1990 | Nason | 422/61 |
| 5,078,968 | 1/1992 | Nason | 422/58 |
| 5,149,506 | 9/1992 | Skiba et al. | 422/102 |
| 5,246,669 | 9/1993 | Hayashi | 422/101 |
| 5,380,492 | 1/1995 | Seymour | 422/101 |
| 5,494,646 | 2/1996 | Seymour | 422/101 |
| 5,514,341 | 5/1996 | Urata et al. | 422/102 |

FOREIGN PATENT DOCUMENTS

| | | |
|---|---|---|
| 0 612 503 A1 | 8/1994 | European Pat. Off. . |
| 8705316 | 6/1987 | Germany . |

OTHER PUBLICATIONS

Patent Abstracts of Japan, vol. 18, No. 450; Aug. 22, 1994, & JP 06 148177 Derwent Publications Ltd., 94–211663.
Patent Abstracts of Japan, vol. 18, No. 530; Oct. 6, 1994, & JP 06 186227.

*Primary Examiner*—Harold Y. Pyon
*Attorney, Agent, or Firm*—Armstrong, Westerman, Hattori, McLeland & Naughton

[57] ABSTRACT

A method for sampling feces, by which an approximately constant amount of feces can be sampled in simple manner and it is possible to easily identify whether occult blood is present in the feces or not. The method comprises a main container for a liquid for suspending feces in it, a cap arranged a one end of said main container, a separating means for dividing inner spaces of the main container and the cap, a through-hole formed in the separating means, and a collecting stick having a means for collecting feces engaged and inserted in the through-hole, wherein the means for collecting feces is composed of a plurality of hairs and arranged at or near the forward end of the collecting stick, whereby feces collected by the means for collecting feces being composed of said plurality of hairs are passed into the through-hole of the separating means in order to sample an approximately constant amount of the feces.

8 Claims, 4 Drawing Sheets

METHOD FOR SAMPLING FECES

BACKGROUND OF THE INVENTION

The present invention relates to a device for sampling feces, by which an approximately constant amount of feces can be sampled and suspended in a liquid to give a preparation for tests in hygienic and simple manner.

Feces are specimens suitable for clinical laboratory tests just as blood and urine specimens used for the tests and offer useful information for diagnosis. Above all, the detection of occult blood in feces is very useful for diagnosis of diseases of digestive organs, in particular, colon cancer, and the detection of occult blood in feces is adopted in mass medical screening and medical checking of elderly subjects. It is now indispensable for the maintenance of health of the people.

As a method for detecting occult blood in feces, chemical method such as guaiac method has been used in the past, while a new method based on the principle of immunological reaction has been developed in recent years. Since this method is superior to chemical method in terms of specificity and sensitivity, the method for detecting occult blood in feces is getting increasingly important. In the detection of occult blood in feces based on immunological measuring method, it is necessary that an approximately constant amount of feces is sampled and suspended in a suitable liquid. In this respect, there are now strong demands on the development of a device for sampling feces, which has the above functions and does not require the use of other devices and which can be used in simple and hygienic manner and has no need to wipe off the attached feces during collecting of the feces.

As a device for sampling feces to attain the above purposes, a conventional type device for sampling feces as shown in FIG. 5 has been known, which comprises a dripping portion 1 at the lower end, a main container 3 with a liquid 2 in it, a cap 4 placed on the main container 3, a collecting stick 5 mounted on the cap 4, a rubber plug 6 fixed in the main container, and a through-hole 7 formed in the rubber plug 6 to accommodate the collecting stick 5 through it, wherein spiral grooves 8 to collect feces are provided at the forward end of the collecting stick 5.

However, in the device for sampling feces as described above, since feces are collected by attaching them on the spiral grooves 8, such drawbacks are found that it is difficult to have feces perfectly stuck in the grooves 8 and furthermore only very small quantity of feces can be stuck in the grooves 8, thus making it difficult to collect an approximately constant amount of feces for the tests. For example, in case feces are stuck perfectly in the grooves and are passed through the rubber plug 6, it is possible to have the feces almost evenly stuck in the grooves. However, because persons collecting feces are unskilled in most cases, the spiral grooves 8 are passed through the rubber plug 6 without perfectly filling the grooves 8 with feces. Thus, even when the grooves are passed through the rubber plug 6, some portions of the grooves 8 are not filled with feces, and the quantity of collected feces varies widely.

Furthermore, colon cancer mostly occurs in sigmoid colon or rectum. Because feces pass through sigmoid colon and rectum after they have been produced, surfaces of feces are covered with blood in the cases of sigmoid colon cancer or rectal cancer. When the conventional type collecting stick 5 to collect feces by sticking it into feces is used, it may not be possible to effectively collect surface portions of feces, and hence in the above case it may not be possible to accurately identify whether occult blood is present in the feces or not.

SUMMARY OF THE INVENTION

To solve the above problems, it is an object of the present invention to provide a device for sampling feces, by which it is possible to collect an approximately constant amount of feces for the tests in easy manner and to accurately identify whether occult blood is present or not in feces.

It is another object of the present invention to provide a device for sampling feces, by which it is possible to effectively collect surface portions of the feces.

It is still another object of the present invention to provide a device for sampling feces, by which it is possible to suspend the collected feces in a liquid in easy and reliable manner.

To attain the above objects, the present inventors have found after fervent efforts that it is possible to collect surface portions of feces by using a means for collecting feces of the collecting stick designed in brush or brush-like shape and rolling the means along the surface of the feces. If the means for collecting feces is designed in brush or brush-like shape, even when feces are not attached evenly on the brush or the like, feces are stuck to the brush or the like almost evenly when it is passed into the through-hole, and excessive quantity of feces is removed when passing through the hole.

The device for sampling feces according to the present invention comprises a main container for a liquid for suspending feces in it, a cap arranged on one end of the main container, a separating means for dividing inner spaces of the main container and the cap, a through-hole formed in the separating means, and a collecting stick having a means for collecting feces engaged and inserted into the through-hole, wherein the means for collecting feces is composed of a plurality of brush hairs and arranged at or near the forward end of the collecting stick.

The above and other objects and advantages of the invention will become more apparent from the following description.

DETAILED DESCRIPTION OF THE PREFERRED EMBODIMENT

Figure 1:
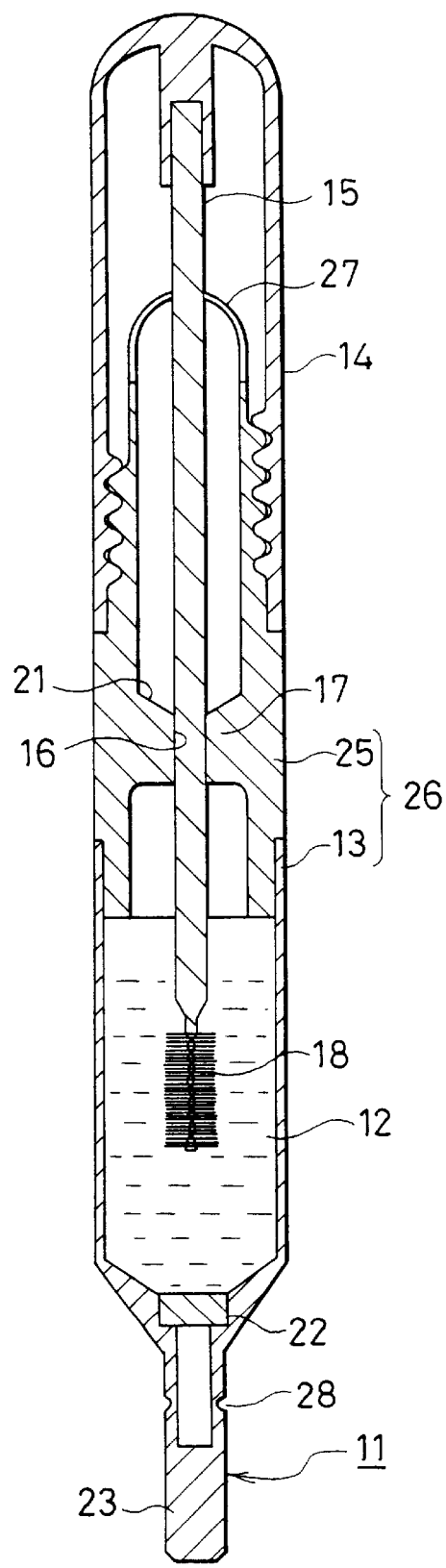
FIG. 1 is a cross-sectional view of an embodiment of the present invention.

In the following, description will be given on an embodiment of the present invention referring to the drawings.

FIG. 1 is a cross-sectional view of an embodiment of the present invention, which has a tapered dripping portion 11 at lower end. On an opening at upper end of a cylindrical container 13, which accommodates a liquid 12 in it, a cylindrical connecting member 25 having openings at two ends and a sparating wall 17 inside is closely engaged, thus forming a cylindrical main container 26. The cylindrical container 13 and the cylindrical connecting member 25 may be integrated together to form the main container 26.

In the upper opening of the cylindrical connecting member 25, a cylindrical cap 14 is screwed or engaged. At the center of a bottom surface of the cap 14, a collecting stick 15 with circular cross-section is closely fitted and fixed.

As shown in FIG. 1, the collecting stick 15 is slidably engaged in a through-hole 16, which has cylindrical shape and is formed at the middle of the separating wall 17.

Figure 2:
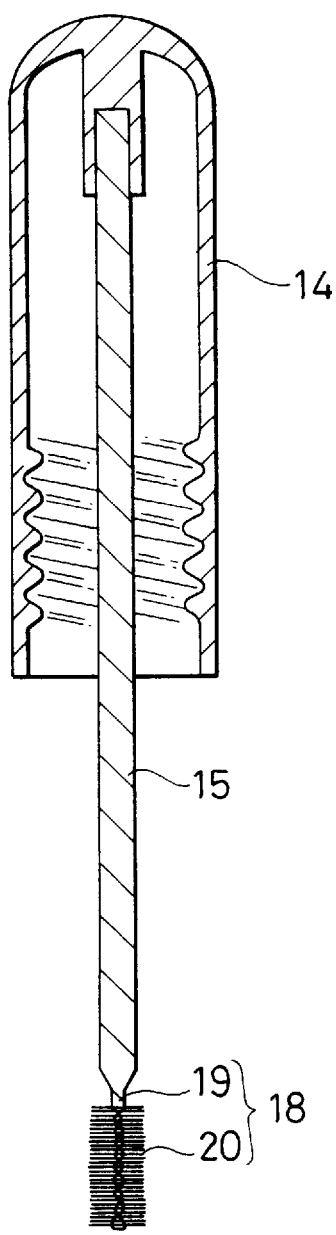
FIG. 2 is a cross-sectional view of a collecting stick in a device of the present invention.

At the forward end of the collecting stick 15, a brush portion 18 as a means for collecting feces is provided. As shown in FIG. 2, the brush portion 18 comprises a wire-like member or a rod-like member 19 connected at the forward end of the collecting stick 15, and on which a plurality of brush hairs 20 for collecting feces are fixed so that external shape formed by connecting tips of brush hairs is approximately in cylindrical shape.

The brush portion 18 is designed in such manner that brush hairs or hair bundles are fixed on it and feces can be collected by rolling the brush over the feces. For example, it may be designed in brush-like shape such as a writing brush or of an ordinary brush.

In the above embodiment, a plurality of brush hairs 20 are attached on outer periphery of the rod-like member 19 in directions perpendicular to axial direction of the rod-like member, i.e. axial direction of the collecting stick so that external shape formed by connecting tips of the hairs is in approximately cylindrical shape, while brush hairs may not be designed in this way. For example, brush hairs running upward, downward or horizontal directions with respect to axial direction of the rod member 19 may be provided independently or in combination. The length of each hair may not be identical, and long hairs and short hairs may be present in mixed manner. Also, the hairs may be provided all over the outer periphery of the rod member or they may be distributed locally more intensively than at other portions. Instead of the rod member, a wire-like member may be used.

Figure 3:
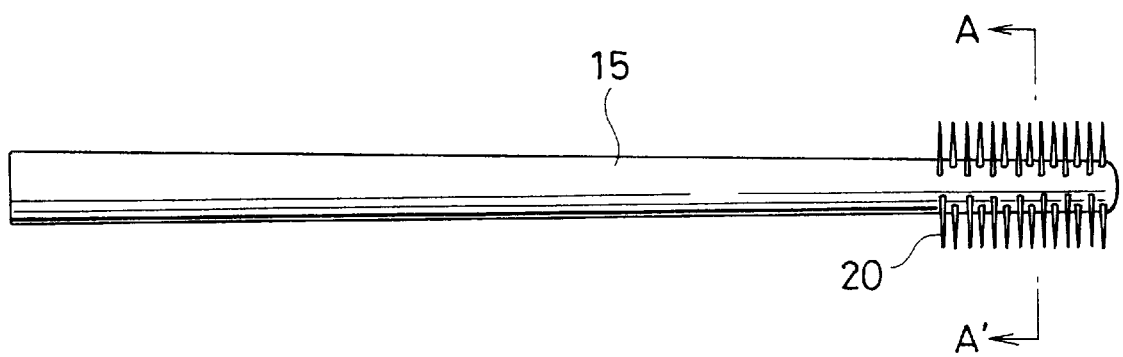
FIG. 3 is a side view of another example of the collecting stick of the present invention.
Figure 4:
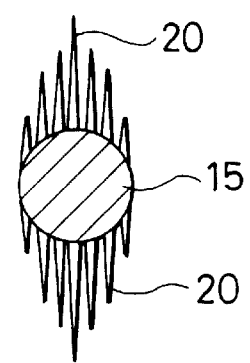
FIG. 4 is a cross-sectional view along the line A–A' of FIG. 3.

FIG. 3 and FIG. 4 each represents another example of the collecting stick of the present invention, where a plurality of hairs 20 are directly provided on the forward end of the collecting stick 15.

In the above embodiment, the hairs 20 are arranged in vertical direction, i.e. upward and downward directions as seen in FIG.4, and the external shape formed by connecting tips of the hairs 20 is in approximately elliptical shape.

When the brush portion 18 is made such as in the examples of FIG. 3 or FIG. 4, by rolling the brush portion 18 on the feces to be collected, not only surface portion of the feces but also inner portion of the feces can be collected. Also, the brush portion mentioned above is convenient when collecting by rolling and collecting by sticking are simultaneously used.

As the material of the hairs 20 used in the present invention, it is preferable to use flexible hairs, while harder material may be used if the hairs 20 can be bent when passing into the through-hole 16. For example, the hairs of such materials as used in a tooth brush may be preferably used.

As the material for the hairs 20 used in the present invention, a synthetic resin such as vinyl resin, acrylic resin or polyamide resin may be used.

In the above embodiment, the upper end of the cylindrical connecting member 25 is designed to have a shape made by cutting diagonally a cylinder as seen in parts 27 in FIG. 1. It is not alway necessary to provide such a shape, while that shape facilitates insertion of the collecting stick 15.

In the above embodiment, the upper surface 21 of the separating wall 17 is inclined in tapered shape toward the through-hole 16. This is not always necessary, but such will facilitate the insertion of the brush portion 18 into the through-hole 16.

The separating wall 17 may be designed as a separate body such as a plug or may be integrated with the cylindrical connecting member 25 or with the cylindrical container 13. In the case where the separating wall 17 is arranged as a separate body, the upper end should be closely fitted and engaged with the upper end of the main container 26.

It is preferable that the separating wall 17 is made of synthetic resin or an elastic material such as rubber, silicone or flexible plastics. In particular, it is preferable that the separating wall 17 is made of an elastic material because the brush portion 18 can be strongly and elastically pressed.

The dripping portion 11 is designed in form of a funnel, and a filter 22 is arranged at the upper end. When the collected feces are suspended in a liquid 12 and filtrate is dripped from the lower end of a leg 23 of the dripping portion 11, a bore may be formed at the lower end of the leg 23 by ordinary procedure or a notch 28 may be provided at an adequate position on the leg 23 and the leg may be broken off at the notch 28.

The filter 22 is arranged to filter insolubles in the solution, in which feces are suspended. The filter is normally arranged inside the container, while it may be arranged outside so that the insolubles in the solution are filtered when the solution is used in occult blood test.

The device for sampling feces according to the present invention may be commercially marketed in the conditions as shown in FIG. 1. In this case, the collecting stick 15 may be designed in such manner that it is closely fitted in the through-hole 16, thus playing a role of a plug. Or, the cap 14 provided with the collecting stick 15 may be arranged separately from the main container 13, and a plug may closely be fitted in the through-hole 16. In this case, it may be so designed that the brush portion 18 is closely passed into the through-hole 16 and the plug may be dropped into the solution.

To increase sealing property of the device for sampling feces of the present invention, an elastic material such as rubber, silicone or flexible plastics may be arranged at a contact portion between the cap 14 and the main container 26. Or, the separating wall 17 may be made of an elastic material mentioned above and may be engaged with the upper end of the main container 26 so that it plays a role of a packing. Alternatively, a packing for this purpose may be arranged at the contact portion.

In order to prevent suspending of excessive quantity of feces attached on the brush portion 18 in the liquid 12, it is preferable that the collecting stick 15 is closely and slidably fitted. To facilitate sliding of the stick, the separating wall 17 is preferably made of an elastic material mentioned above.

Next, description will be given on the procedure to use the device for sampling feces of the present invention with the above arrangement.

With the collecting stick 15 separated from the main container 26 as shown in FIG. 2, surface portions of feces are collected by rolling the outer portion of the brush portion 18 over the feces. In the cases of sigmoid colon cancer or rectal cancer, occult blood caused by these cancers is probably present in the surface portions of the feces. Therefore, by the above procedure, the feces containing blood can be effectively sampled.

Next, the brush portion 18 is closely engaged in the through-hole 16 of the separating wall 17 of the main container 13. Under this condition, the hairs of the brush portion 18 are bent down and are closely fitted in the through-hole 16. The feces are elastically pressed and are stuck into the brush portion evenly, while excessive quantity of feces are pushed upward and are moved toward the upper surface of the separating wall 17.

When the brush portion 18 is immersed into the liquid 12, the hairs 20 of the brush portion 18 rise up vigorously and strike the liquid 12 with strong resilient force. Thus, it is possible to easily suspend the feces attached on the brush portion 18 into the liquid 12.

Figure 5:
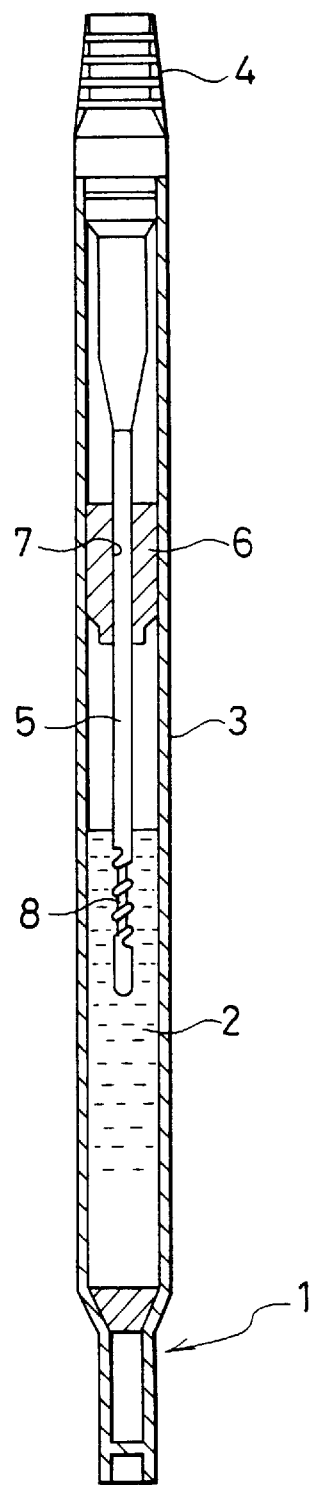
FIG. 5 is a cross-sectional view of a conventional type device for sampling feces.

In the collecting stick of the conventional type device as shown in FIG. 5, feces may not be easily suspended in the liquid 12. In the present invention, the feces attached on the brush portion 18 can be easily and perfectly suspended in the liquid 12 if necessary by shaking because feces are present not as a big mass and, therefore, feces have a large contact surface area.

In this way, the feces suspended in the liquid 12 can be carried to the site of examination. Once brought to the site of examination, filtrate of feces suspended solution can be dripped from the lower end of the dripping portion through the filter 22 by an ordinary procedure and are applied to the examination.

The collecting stick 15 of the present invention may be stuck into the feces, in place of rolling on the feces to collect samples as in the past. Even in this case, to sample an approximately constant amount of the feces can be performed more effectively than in the conventional procedure.

As described above, it is possible according to the present invention to effectively collect surface portions of the feces because a plurality of hairs are arranged on the means for collecting feces. This makes it possible to facilitate accurate examination of colon cancer. Because feces can be sampled more uniformly and effectively on said plurality of brush hairs than in conventional way of sampling in the grooves, the better quantitative sampling can be carried out, and the collected feces can be easily and perfectly suspended in the liquid. This facilitates easy and simple examination for the diagnosis of colon cancer and can provide such a remarkable effect as not found in the conventional device for sampling feces.

What is claimed is:

1. A method for collecting a feces sample and for preparing a suspension of feces in a liquid, comprising:

providing a sampling device comprising
a feces collector including a feces collecting rod having a plurality of hairs formed on or near a tip of the collecting rod and extending radially outwardly from the collecting rod, and a container defining an internal space accommodating the liquid, the container having separating means formed with a through-hole having a dimension smaller than the radial outward extension of the hairs, rolling said hairs of said feces collecting rod over a surface of the feces to collect a feces on said hairs, inserting said feces collecting rod with said feces collected thereon through the through-hole of the separating means of the container to thereby lay down said plurality of hairs and push excessive feces upwardly, a feces sample being retained on said feces collecting rod almost quantitatively, and to erect said plurality of hairs vertically after passage through said through-hole, and, suspending said feces sample retained on said collecting rod after passage through the through-hole in the liquid contained in the internal space of the container.

2. A method for collecting a feces sample according to claim 1, wherein said plurality of hairs are in a form of a brush or a brush shape.

3. A method for collecting a feces sample according to claim 1, wherein said plurality of hairs are arranged in directions perpendicular to or downward to an axial direction of said collecting stick.

4. A method for collecting a feces sample according to claim 1, wherein said feces collecting rod is a wire member or a rod member, on which said plurality of hairs are arranged.

5. A method for collecting a feces sample according to claim 4, wherein said plurality of hairs are arranged evenly over the entire outer periphery or distributed locally unevenly on said wire member or rod member.

6. A method for collecting a feces sample according to claim 1, wherein an external shape formed by connecting tips of said plurality of hairs is in approximately cylindrical or elliptical shape.

7. A method for collecting a feces sample according to claim 1, wherein a dripping portion having a filter is provided on an end of said container and liquid having feces suspended therein is filtered through said filter to produce a filtrate.

8. A method for collecting a feces sample according to claim 1, wherein said separating means is a separating wall arranged on inner peripheral surface of the container and is made of an elastic material.

* * * * *